(12) United States Patent
Shue et al.

(10) Patent No.: US 6,921,386 B2
(45) Date of Patent: Jul. 26, 2005

(54) INTRAVENOUS CATHETER INSERTING DEVICE

(76) Inventors: Ming-Jeng Shue, No. 14, Lane 8, Chung-I St., Hsi Dist., Taichung City (TW); Phillip Shue, 7F-2, No. 5, Sec. 3, Lin-Chun E. St., Chung Dist., Taichung City (TW); Deborah Huang, 7F-2, No. 5, Sec. 3, Liu-Chun E. St., Chung Dist., Taichung City (TW)

( * ) Notice: Subject to any disclaimer, the term of this patent is extended or adjusted under 35 U.S.C. 154(b) by 314 days.

(21) Appl. No.: 10/388,984

(22) Filed: Mar. 14, 2003

(65) Prior Publication Data

US 2004/0106903 A1 Jun. 3, 2004

(30) Foreign Application Priority Data

Dec. 2, 2002 (TW) ........................................ 91134962 A

(51) Int. Cl.[7] .......................... A61M 5/178; A61M 5/00
(52) U.S. Cl. .................... 604/164.01; 604/110
(58) Field of Search .............................. 604/93.01, 110, 604/162, 164.01, 164.07, 164.08, 164.09, 165.01, 171, 187, 192, 197, 218, 240, 263, 264, 272, 533

(56) References Cited

U.S. PATENT DOCUMENTS

| | | | | |
|---|---|---|---|---|
| 5,129,884 A | * | 7/1992 | Dysarz | 604/164.08 |
| 5,575,777 A | * | 11/1996 | Cover et al. | 604/198 |
| 5,702,367 A | * | 12/1997 | Cover et al. | 604/110 |
| 5,817,058 A | * | 10/1998 | Shaw | 604/110 |
| 5,911,705 A | * | 6/1999 | Howell | 604/110 |
| 5,989,220 A | * | 11/1999 | Shaw et al. | 604/110 |

* cited by examiner

*Primary Examiner*—Nicholas D. Lucchesi
*Assistant Examiner*—Mark K. Han
(74) *Attorney, Agent, or Firm*—Woodard, Emhardt, Moriarty, McNett & Henry, LLP

(57) ABSTRACT

An intravenous catheter inserting device includes a catheter hub engaging an open forward end of a barrel and having a duct that communicates with a passage of the barrel. A tubular catheter is disposed to communicate with the duct, and permits a needle cannula to pass therethrough. A plunger is received in the passage and extends rearwardly of the barrel so as to be manually operable. The plunger has a cavity containing fluid at a reduced pressure, and is coupled with the needle cannula within the passage such that the needle cannula can be retracted into the cavity due to a pressure difference between the ambient air and the reduced pressure.

17 Claims, 13 Drawing Sheets

INTRAVENOUS CATHETER INSERTING DEVICE

BACKGROUND OF THE INVENTION

1. Field of the Invention

This invention relates to an intravenous catheter inserting device, more particularly to an intravenous catheter inserting device which enables a needle cannula to be retracted within a plunger cavity having a reduced pressure therein.

2. Description of the Related Art

Intravenous catheter inserting devices are generally used to administer medication fluid into or draw blood from a patient's vein. Referring to FIGS. 1 and 2, a conventional intravenous catheter inserting device 1 is shown to include a tubular needle seat 11 with a hub end 111, a needle cannula 12 secured to the hub end 111, a catheter hub 13 sleeved on the needle seat 11, and a flexible tubular catheter 14 secured to the catheter hub 13. In use, the catheter 14 and the needle cannula 12 are inserted into the patient's vein by a health care worker by piercing the patient's vein with a sharp tip of the needle cannula 12 which projects outwardly of the catheter 14. The health care worker then withdraws the needle cannula 12 from the catheter 14 with one hand and, at the same time, applies pressure to the patient's skin with the other hand, thereby leaving the catheter 14 in the patient's vein. Subsequently, a transfusion member (not shown) with medication fluid or an empty barrel is connected to the catheter hub 13 for administering the medication fluid into the patient's vein or for drawing blood. At this time, as the health care worker must place the used needle cannula 12 and the needle seat 11 on a tray (not shown) nearby, the exposed sharp tip of the used needle cannula 12 may create a danger of an accidental needle stick. Moreover, blood contamination may occur during connection of the catheter hub 13 to the transfusion member or the empty barrel.

Referring to FIG. 2, during the insertion procedure, the flow of blood into the catheter 14 through a notch 121 in the needle cannula 12 can be observed through the translucent catheter 14. However, due to the presence of the notch 121, the needle cannula 12 tends to be bent during passage of the catheter 14 into the patient's vein. In addition, the blood in the catheter 14 is not visible when the portion of the needle cannula 12 with the notch 121 is inserted into the patient's vein.

SUMMARY OF THE INVENTION

The object of the present invention is to provide an intravenous catheter inserting device which can prevent accidental, inadvertent contact with a needle cannula after use, and which can prevent contamination of that was drawn with the use of the same.

According to this invention, the intravenous catheter inserting device includes a catheter hub, a tubular catheter, a barrel, a needle cannula, a tubular needle seat, and a plunger.

The catheter hub includes a surrounding tip wall which surrounds a first axis and which confines a through hole, a sleeve wall which has an inner sleeve wall surface that confines an insert hole larger than the through hole, and an intermediate tubular wall which is interposed between the surrounding tip wall and the sleeve wall, which confines a duct communicating the insert hole with the through hole, and which has a communicating port to communicate the duct with ambient air.

The tubular catheter includes a proximate segment which is disposed in the through hole and which extends along the first axis to communicate with the duct, and a distal segment which extends from the proximate segment along the first axis to project outwardly of the surrounding tip wall.

The barrel has outer and inner surrounding barrel wall surfaces opposite to each other and surrounding a second axis. The inner surrounding barrel wall surface confines a passage which has opposite open forward and rearward ends, and includes a larger-diameter segment and a smaller-diameter segment that confine rear and front passageways, respectively, and that are disposed proximate to the open rearward and forward ends, respectively, to form a surrounding shoulder portion. The outer surrounding barrel wall surface has a front surrounding region which is secured relative to the inner sleeve wall surface, thereby resulting in coincidence of the first axis with the second axis.

The needle cannula includes opposite tip and fixed ends and a middle segment interposed therebetween.

The tubular needle seat is received in the passage, and extends along the second axis. The tubular needle seat includes a hub end which is disposed to secure the fixed end, a surrounding engaged wall which extends from the hub end along the second axis and which confines an axial path to accommodate or communicate with the fixed end, and an anchoring segment which confines an axial through hole to communicate with the passage and which extends outwardly of the front passageway from the surrounding engaged wall. The surrounding engaged wall has an outer engaged wall surface which engages the smaller-diameter segment and which is rotatable relative to the smaller-diameter segment about the second axis between interengaged and released positions, where the surrounding engaged wall is respectively unmovable and movable relative to the smaller-diameter segment along the second axis, respectively. The anchoring segment terminates at an anchoring end which is rotated with the surrounding engaged wall. As such, when the surrounding engaged wall is turned in a clockwise direction from the interengaged position to the released position, the anchoring end can move from a hook-up position that is closer to the surrounding shoulder portion, to a depressed position that is remote from the surrounding shoulder portion.

The plunger is received in the passage such that in a use position, the plunger is movable along the larger-diameter segment, and such that in a disposal position, the plunger is unmovable along but is rotatable relative to the larger-diameter segment. The plunger includes a plunger body and a seal member.

The plunger body includes a top end wall disposed to confront the surrounding shoulder portion, and a bottom end wall extending outwardly of the open rearward end to permit movement and rotation of the plunger. The top end wall has an inner peripheral edge portion which surrounds the second axis, and which defines a cavity therein. The cavity extends along the second axis and towards the bottom end wall, and contains fluid at a reduced pressure.

The seal member includes an anchored portion and a sealing portion. The anchored portion is disposed to be engageable with the anchoring end such that when the plunger is in the disposal position, and when the surrounding engaged wall is in the interengaged position, rotation of the plunger body in a clockwise direction relative to the larger-diameter segment brings the surrounding engaged wall to turn from the interengaged position to the released position, thereby moving the anchoring end from the hook-up position to the depressed position. The sealing portion is sealingly attached to the inner peripheral edge portion along a sealing line so as to trap the fluid in the cavity. Movement of the anchoring end from the hook-up position to the depressed position results in depression of the anchored portion so as to rip the sealing line, thereby releasing the seal member from the plunger body. Hence, the tubular needle seat together with the needle cannula can be pulled by the seal member which is suctioned into the cavity due to a pressure difference between the reduced pressure and the ambient air that is introduced through the communicating port, thereby permitting retraction of the needle cannula from the tubular catheter into the cavity.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
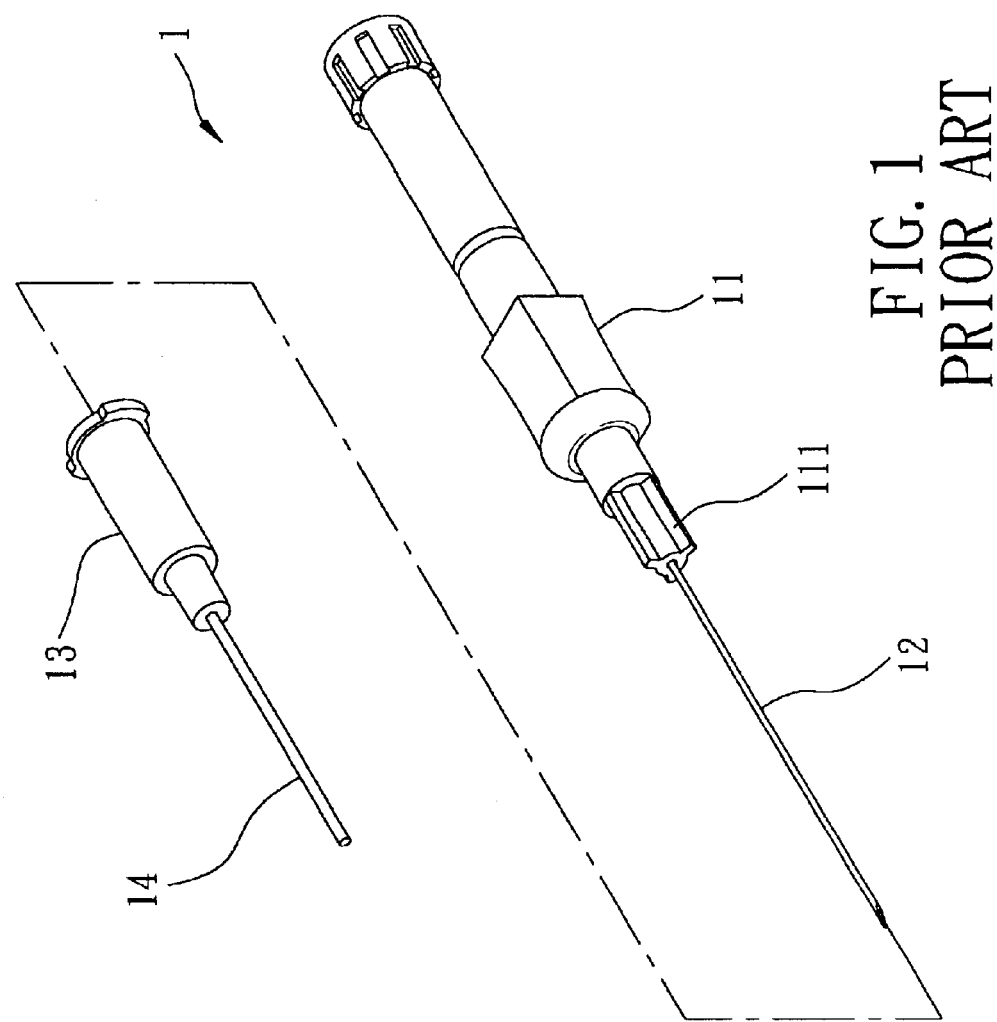
FIG. 1 is a perspective view of a conventional intravenous catheter inserting device.
Figure 2:
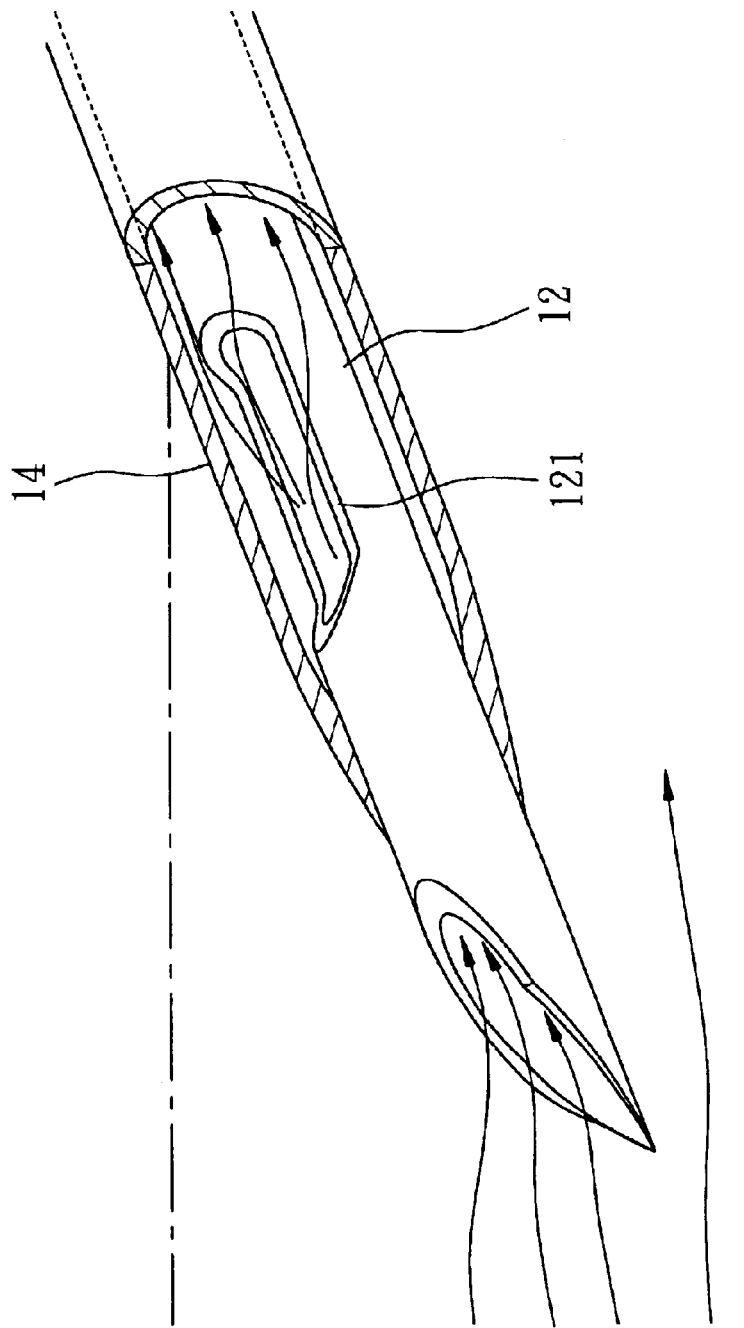
FIG. 2 is a partly sectional schematic view illustrating a needle cannula sleeved over by a catheter of the conventional intravenous catheter inserting device.

Before the present invention is described in greater detail, it should be noted that same reference numerals have been used to denote like elements throughout the specification.

Figure 3:
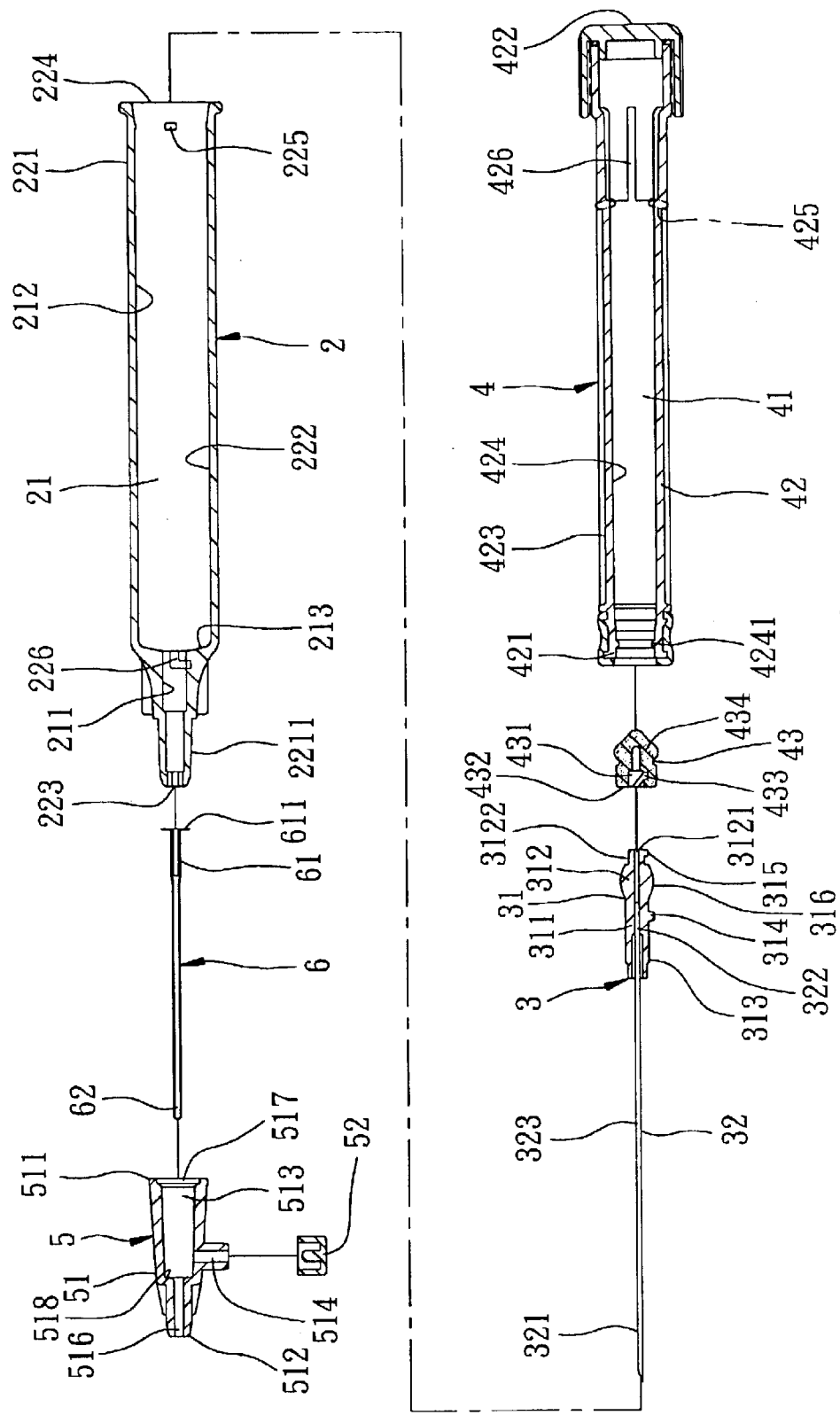
FIG. 3 is an exploded sectional view of the first preferred embodiment of an intravenous catheter inserting device according to this invention.
Figure 4:
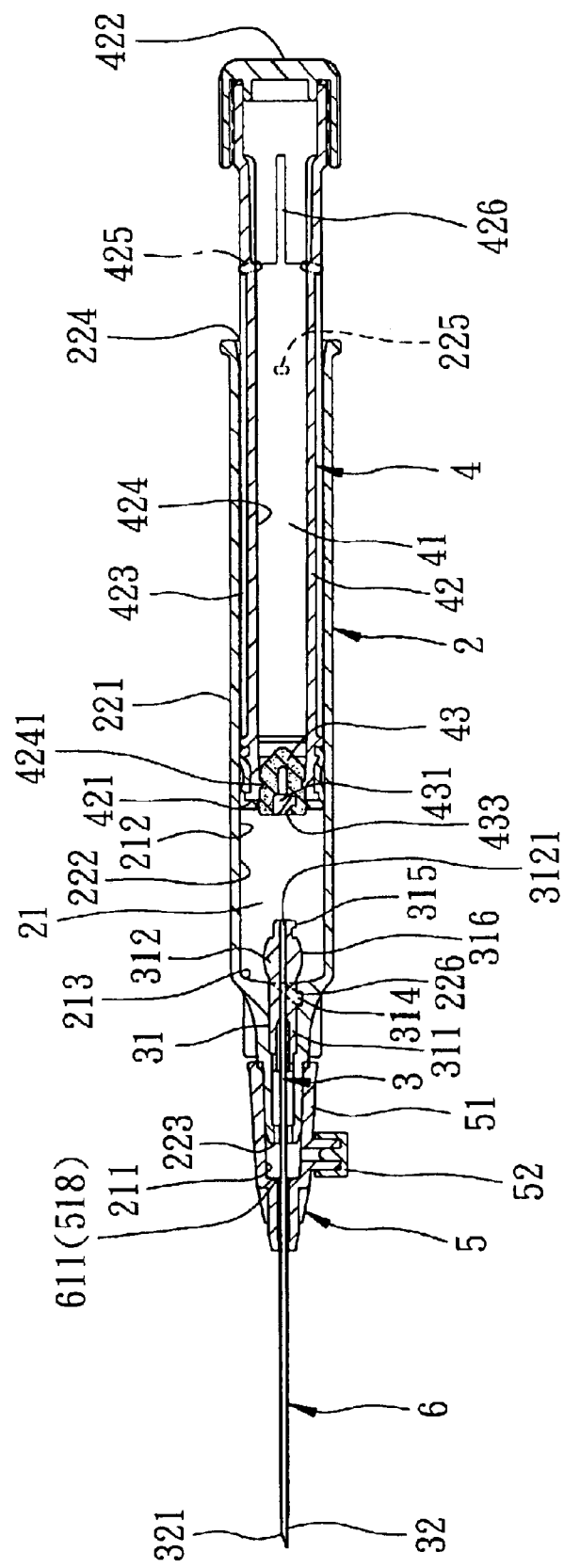
FIG. 4 is a sectional view of the first preferred embodiment in a state of use.

Referring to FIGS. 3 and 4, the first preferred embodiment of an intravenous catheter inserting device according to the present invention is shown to comprise a catheter hub 5, a tubular catheter 6, a barrel 2, a needle assembly 3, and a plunger 4.

The catheter hub 5 includes a surrounding tip wall 512, a sleeve wall 511 which is opposite to the surrounding tip wall 512 along a first axis, and an intermediate tubular wall 51 which is interposed between the surrounding tip wall 512 and the sleeve wall 511.

The surrounding tip wall 512 surrounds the first axis, and confines a through hole 516 which extends along the first axis. The sleeve wall 511 has an inner sleeve wall surface which surrounds the first axis and which confines an insert hole 517 larger than the through hole 516. The intermediate tubular wall 51 has an inner tubular wall surface that confines a duct 513 which communicates the insert hole 517 with the through hole 516, and an outer tubular wall surface opposite to the inner tubular wall surface in radial directions. In addition, the intermediate tubular wall 51 has a communicating port 514 which extends radially through the inner and outer tubular wall surfaces to communicate the duct 513 with ambient air. A plug 52 is disposed to close the communicating port 514, as shown in FIG. 4. The inner tubular wall surface of the intermediate tubular wall 51 forms a retaining shoulder 518 with the surrounding tip wall 512. The retaining shoulder 518 confronts the duct 513 along the first axis.

The tubular catheter 6 includes a proximate segment 61 which is disposed in the through hole 516 and which extends along the first axis to communicate with the duct 517 and to project outwardly of the through hole 516, and a distal segment 62 which extends from the proximate segment 61 along the first axis to project outwardly of the surrounding tip wall 512. The proximate segment 61 terminates at a flange portion 611 which abuts against and which is retained at the retaining shoulder 518.

The barrel 2 has outer and inner surrounding barrel wall surfaces 221,222 opposite to each other and surrounding a second axis. The inner surrounding barrel wall surface 222 confines a passage 21 which has open forward and rearward ends 223,224 that are disposed opposite to each other in a longitudinal direction parallel to the second axis, and includes a larger-diameter segment 212 and a smaller-diameter segment 211 which confine rear and front passageways, respectively, and which are disposed proximate to the open rearward and forward ends 224,223, respectively, to form a surrounding shoulder portion 213 between the larger-diameter segment 212 and the smaller-diameter segment 211. The outer surrounding barrel wall surface 221 has a front surrounding region 2211 which is proximate to the open forward end 223, and which is insertable into the insert hole 517 so as to abut against the inner sleeve wall surface of the sleeve wall 511, thereby resulting in coincidence of the first axis with the second axis. A first female screw thread segment 225 includes a plurality of angularly displaced ribs, and is disposed on the larger-diameter segment 212 adjacent to the open rearward end 224. A second female screw thread segment 226 in the form of a spiral groove is disposed on the smaller-diameter segment 211 adjacent to the surrounding shoulder portion 213.

The needle assembly 3 includes a needle cannula 32 and a tubular needle seat 31.

The needle cannula 32 includes tip and fixed ends 321,322 opposite to each other, and a middle segment 323 interposed between the tip and fixed ends 321,322.

The tubular needle seat 31 is made of a light transmissible material, is received in the passage 21, and extends along the second axis. The tubular needle seat 31 includes a hub end 313 which is disposed to secure the fixed end 322 of the needle cannula 32, and a surrounding engaged wall 311 which extends from the hub end 313 along the second axis, and which confines an axial path to accommodate or communicate with the fixed end 322 of the needle cannula 32. The surrounding engaged wall 311 has an outer engaged wall surface which is provided with a (second) male screw thread segment 314 that includes a plurality of angularly displaced ribs and that surrounds the second axis to threadedly engage the second female screw thread segment 226 in an interengaged position, whereby the surrounding engaged wall 311 of the tubular needle seat 31 is unmovable relative to the smaller-diameter segment 211 along the second axis.

The tubular needle seat 31 further includes an anchoring segment 312 which confines an axial through hole 3121 to communicate with the passage 21, and which extends outwardly of the front passageway of the smaller-diameter segment 211 from the surrounding engaged wall 311 to terminate at an anchoring end 3122. A (third) male screw thread segment 315 includes a plurality of ribs and is disposed on the anchoring end 3122.

Figure 5:
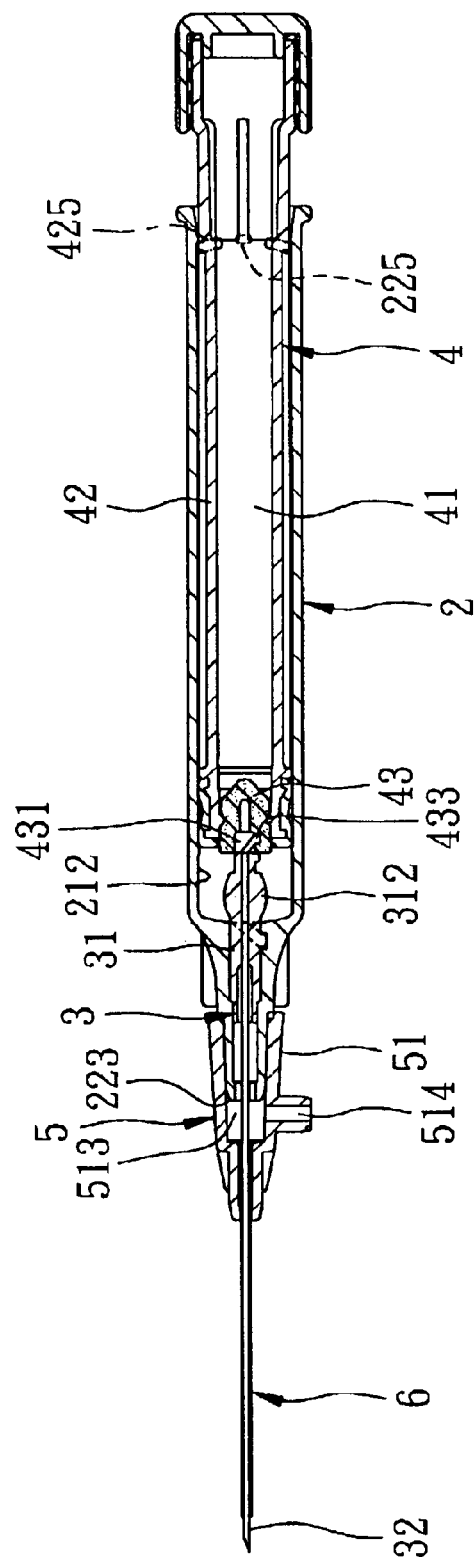
FIG. 5 is a sectional view of the first preferred embodiment in a state where a seal member is in contact with a tubular needle seat.

The plunger 4 is received in the passage 21 such that in a use position, as shown in FIG. 4, the plunger 4 is movable along the larger-diameter segment 212 in the longitudinal direction, and such that in a disposal position, as shown in FIG. 5, the plunger 4 is unmovable along, but is rotatable relative to the larger-diameter segment 212. The plunger 4 includes a plunger body 42 and a seal member 43.

The plunger body 42 includes a top end wall 421 which is disposed to confront the surrounding shoulder portion 213, and a bottom end wall 422 opposite to the top end wall 421 in the longitudinal direction. The bottom end wall 422 extends outwardly of the open rearward end 224 to permit movement and rotation of the plunger 4. The top end wall 421 has an inner peripheral edge portion 424 which surrounds the second axis, and which defines a cavity 41 therein. The cavity 41 extends along the second axis and towards the bottom end wall 422, and contains fluid at a reduced pressure. In addition, the plunger body 42 has an outer plunger wall surface 423 which surrounds the second axis. A first male screw thread segment 425 includes a plurality of ribs, and is disposed on the outer plunger wall surface 423. A catcher portion 426 is disposed on the inner peripheral edge portion 424 proximate to the bottom end wall 422.

The seal member 43 is formed from an elastomeric material, and includes an anchored portion 432 and a sealing portion 434. The anchored portion 432 has an inner surrounding wall which extends along the second axis to confine a recess 431 that is configured to accommodate and to be engageable with the anchoring end 3122 of the anchoring segment 312. The inner surrounding wall is formed with a third female screw thread segment 433 that is in the form of a spiral groove. Referring to FIG. 4, a surrounding protrusion 4241 is disposed to extend from the inner peripheral edge portion 424 in a radial direction and towards the second axis so as to be in frictional contact with the sealing portion 434, thereby establishing a sealing line to trap the fluid in the cavity 41.

In use, as shown in FIG. 4, a health care worker holds the barrel 2 with one hand to insert the tip end 321 of the needle cannula 32 and the distal segment 62 of the tubular catheter 6 into the patient's vein. The anchoring segment 312 of the tubular needle seat 31 is light transmissible and has a convex surface 316 to provide a magnified view of the blood flowing through the axial through hole 3121. Once the health care worker notes that the blood does not flow into the anchoring segment 312, he/she can pull the plunger 4 slightly rearward to draw the blood until the blood is visible through the anchoring segment 312 so as to confirm correct insertion of the tubular catheter 6 into the patient's vein.

Figure 6:
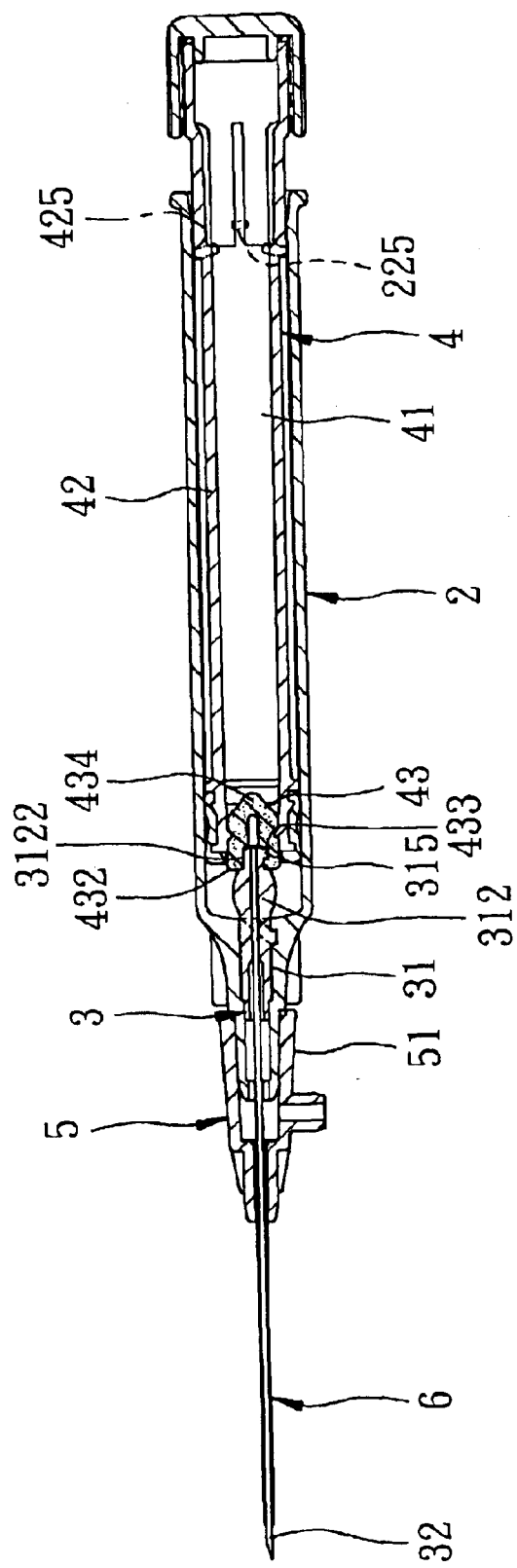
FIG. 6 is a sectional view of the first preferred embodiment in a state where the seal member engages the tubular needle seat.

Referring to FIGS. 5 and 6, the plug 52 shown in FIG. 4 is removed from the communicating port 514 so as to communicate the duct 513 with the ambient air. The plunger 4 is pressed forwardly to contact the tubular needle seat 31 (see FIG. 5). By means of the first male and female screw thread segments 425,225, displacement of the plunger 4 along the larger-diameter segment 212 is restrained, whereas rotation of the plunger 4 in a clockwise direction relative to the larger-diameter segment 212 is permitted. The plunger 4 is screwed toward the open forward end 223. By the screw movement of the plunger 4, the seal member 43 is rotated relative to the tubular needle seat 31, and the anchored portion 432 of the seal member 43 is brought to engage the anchoring end 3122 by virtue of the engagement of the third male and female screw thread segments 315,433, as shown in FIG. 6. Thus, the tubular needle seat 31 is rotatable together with the seal member 43.

Figure 7:
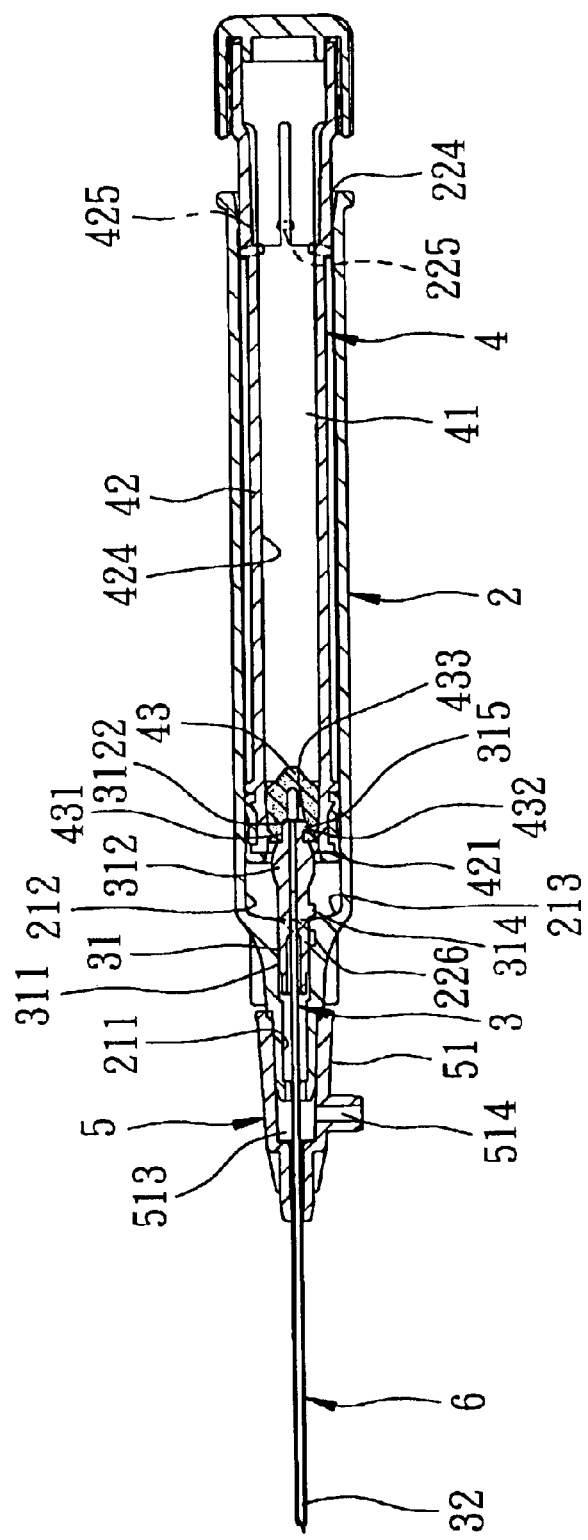
FIG. 7 is a sectional view of the first preferred embodiment in a state where the seal member is disengaged from a plunger body.
Figure 8:
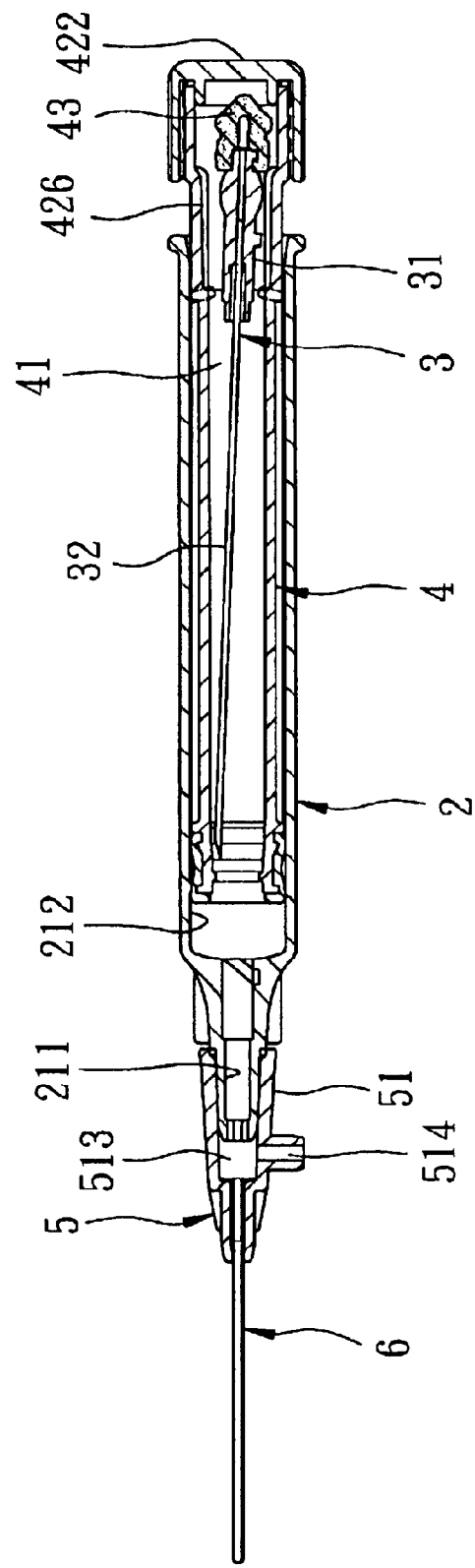
FIG. 8 is a sectional view of the first preferred embodiment in a state where the tubular needle seat and a needle cannula are retracted into the plunger body.

Subsequently, as shown in FIG. 7, when the plunger 4 is further rotated in the clockwise direction relative to the larger-diameter segment 212 such that the tubular needle seat 31 is rotated to turn the second male screw thread segment 314 about the second axis to a released position for removal from the second female screw thread segment 226, the surrounding engaged wall 311 of the tubular needle seat 31 is moved relative to the smaller-diameter segment 211 along the second axis towards the open rearward end 224. The anchoring end 3122 is also rotated to move from a hook-up position that is closer to the surrounding shoulder portion 213 to a depressed position that is remote from the surrounding shoulder portion 213. At the same time, movement of the anchoring end 3122 from the hook-up position to the depressed position will result in depression of the anchored portion 432 so as to rip the sealing line, thereby releasing the seal member 43 from the plunger body 42. As such, the tubular needle seat 31 together with the needle cannula 32 can be pulled by the seal member 43 that is suctioned into the cavity 41 due to the pressure difference between the reduced pressure and the ambient air that is introduced through the communicating port 514, thereby permitting retraction of the needle cannula 32 from the tubular catheter 6 into the cavity 41, as shown in FIG. 8. Furthermore, by means of the catcher portion 426, the tubular needle seat 31 as well as the needle cannula 32 can be prevented from impinging upon the bottom end wall 422.

Figure 9:
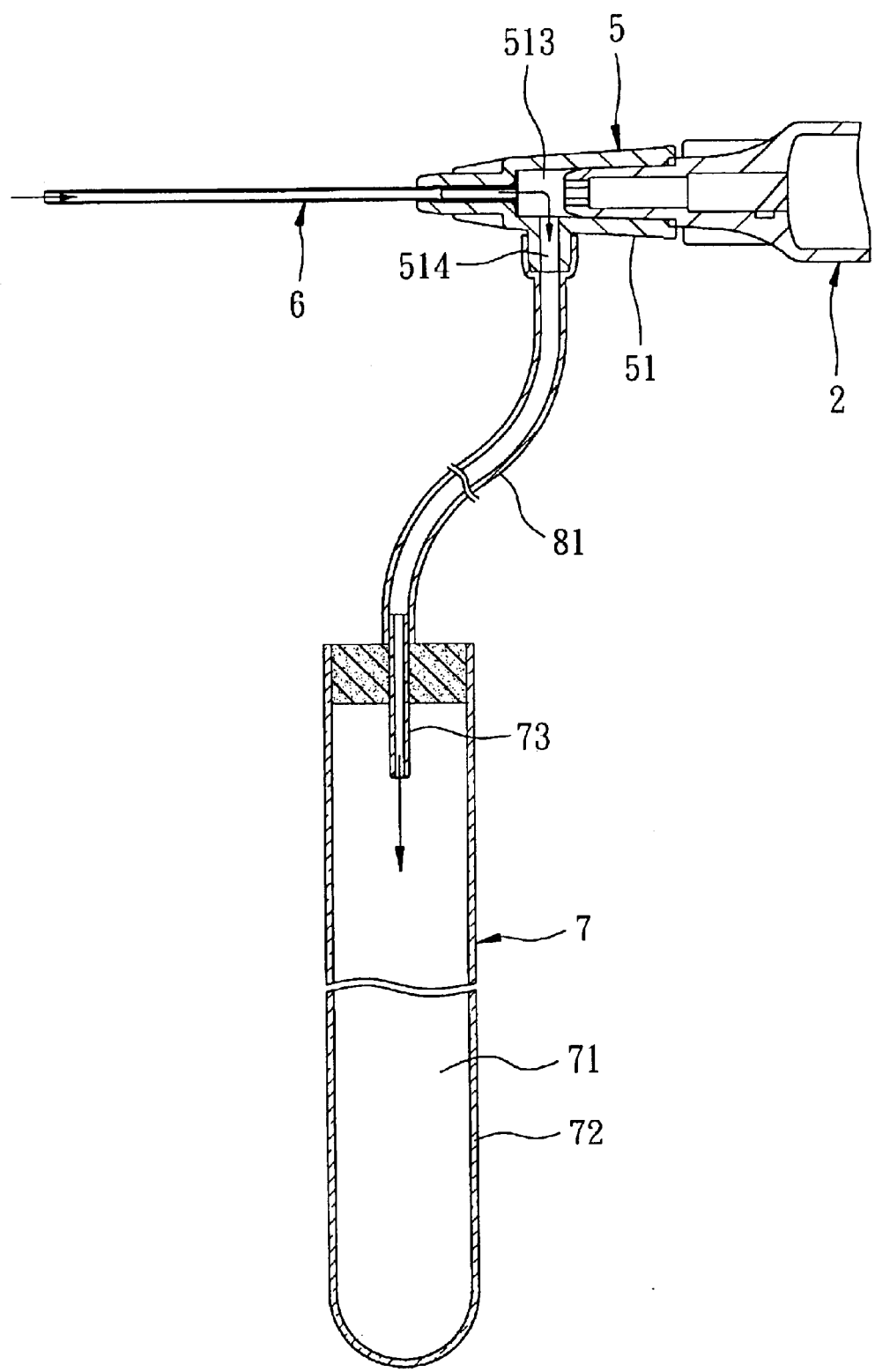
FIG. 9 is a fragmentary sectional view of the first preferred embodiment in another state of use.

Therefore, in use, the health care worker can close the communicating port 514 with the plug 52, and then pull the plunger body 42, in which the seal member 43 and the needle assembly 3 are left, towards the open rearward end 224 so as to draw a smaller amount of blood into the passage 21 of the barrel 2 through the tubular catheter 6. Referring to FIG. 9, when the health care worker needs to draw a larger amount of blood, a blood collecting member 7 is connected to the catheter hub 5. The blood collecting member 7 includes a surrounding wall 72 which confines a receiving space 71 and which has an introduced port 73 communicating with the receiving space 71. A first connecting flexible tube 81 is disposed to interconnect the introduced port 73 and the communicating port 514. The blood can flow into the blood collecting member 7 through the tubular catheter 6, the duct 513, and the first connecting flexible tube 81 without the need to pull the plunger body 42, thereby preventing the health care worker from coming into contact with the blood.

Figure 10:
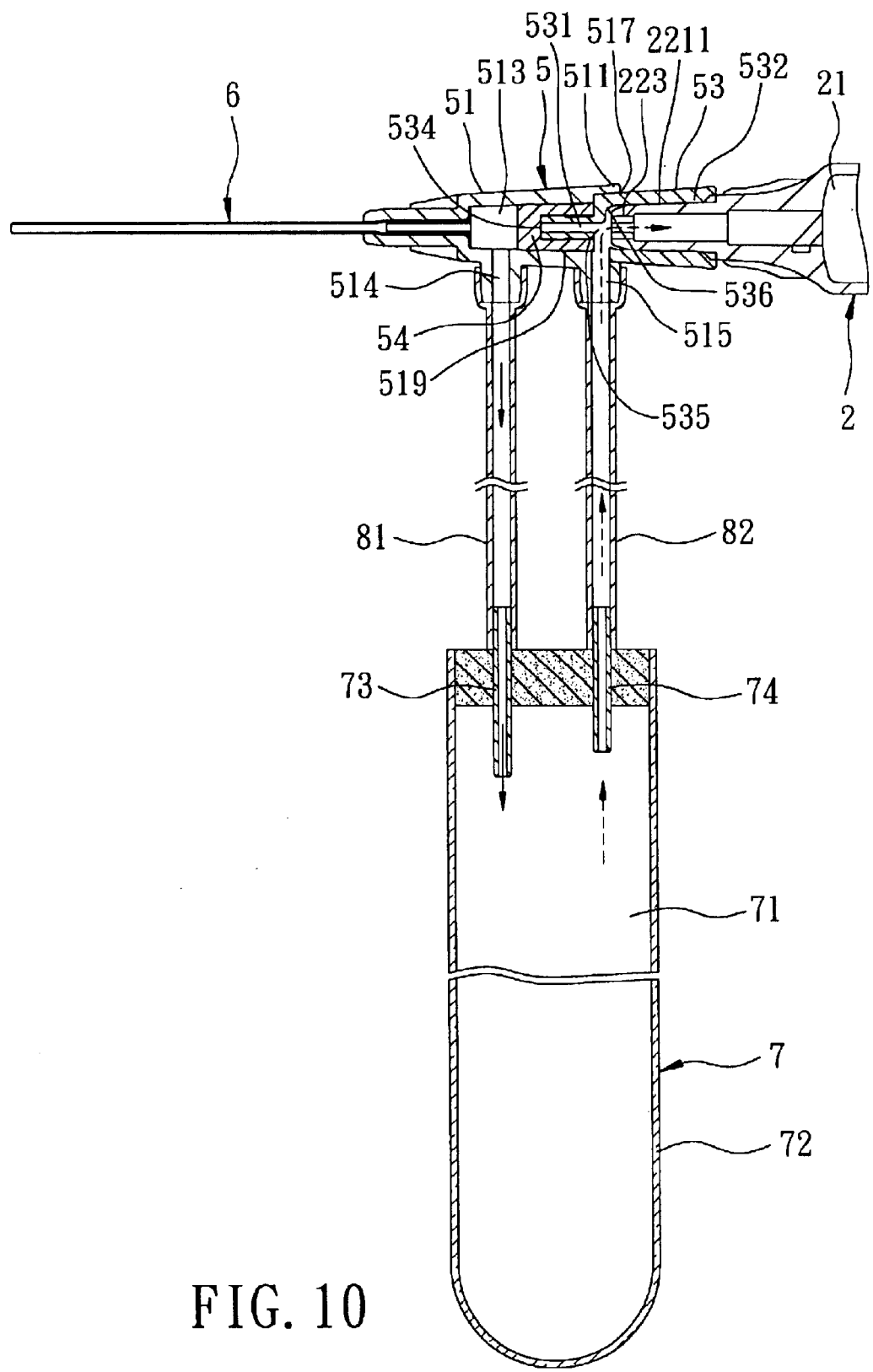
FIG. 10 is a fragmentary sectional view of the second preferred embodiment of an intravenous catheter inserting device according to this invention.

Alternatively, referring to FIG. 10, the second preferred embodiment of the intravenous catheter inserting device according to this invention is shown to be similar to the previous embodiment in construction. In addition to the component parts of the previous embodiment, the inner sleeve wall surface of the sleeve wall 511 of the catheter hub 5 has a reentry port 515 which extends radially through the sleeve wall 511 to communicate with the insert hole 517, and which is opposite to the communicating port 514 relative to a boundary area 519. Moreover, the intravenous catheter inserting device of this embodiment further includes a barrier member 54 and a tubular insert 53. The barrier member 54 is formed from an elastomeric material, such as a rubber. The tubular insert 53 has a front neck end 534 which is connected to the barrier member 54 and which confines a through way 531 along the first axis, and a rear flared end 532 which extends from the front neck end 534 along the first axis, and which has an inner abutted surface 536. The inner abutted surface 536 surrounds the first axis, and confines a fluid path 535 which extends to communicate with the reentry port 515. Furthermore, the blood collecting member 7 has an air outlet 74 spaced apart from the introduced port 73. A second connecting flexible tube 82 is disposed to interconnect the air outlet 74 and the reentry port 515. In assembly, the barrier member 54, on which the front neck end 534 is connected, is engaged with the inner sleeve wall surface of the sleeve wall 511 of the catheter hub 5 at the boundary area 519. The front surrounding region 2211 of the barrel 2 is engaged with the inner abutted surface 536 of the tubular insert 53, thereby aligning the through way 531 with the passage 21 of the barrel 2. The needle cannula 32 (not shown in FIG. 10) extends through the through way 531, a slit in the barrier member 54, the duct 513, and the tubular catheter 6. After the used needle assembly 3 (not shown in FIG. 10) has been retracted into the plunger body (not shown in FIG. 10) in the same manner as described above, the slit in the barrier member 54 is closed by means of its elastomeric material property.

As such, due to the arrangement of the barrier member 54, once it is noted that blood cannot flow into the blood collecting member 7, the health care worker can pull the plunger body 42 rearwardly so as to introduce an air flow from the air outlet 74 through the second connecting flexible tube 82, the reentry port 515, and the fluid path 535 to the passage 21 of the barrel 2, thereby facilitating blood flow into the blood collecting member 7.

Figure 11:
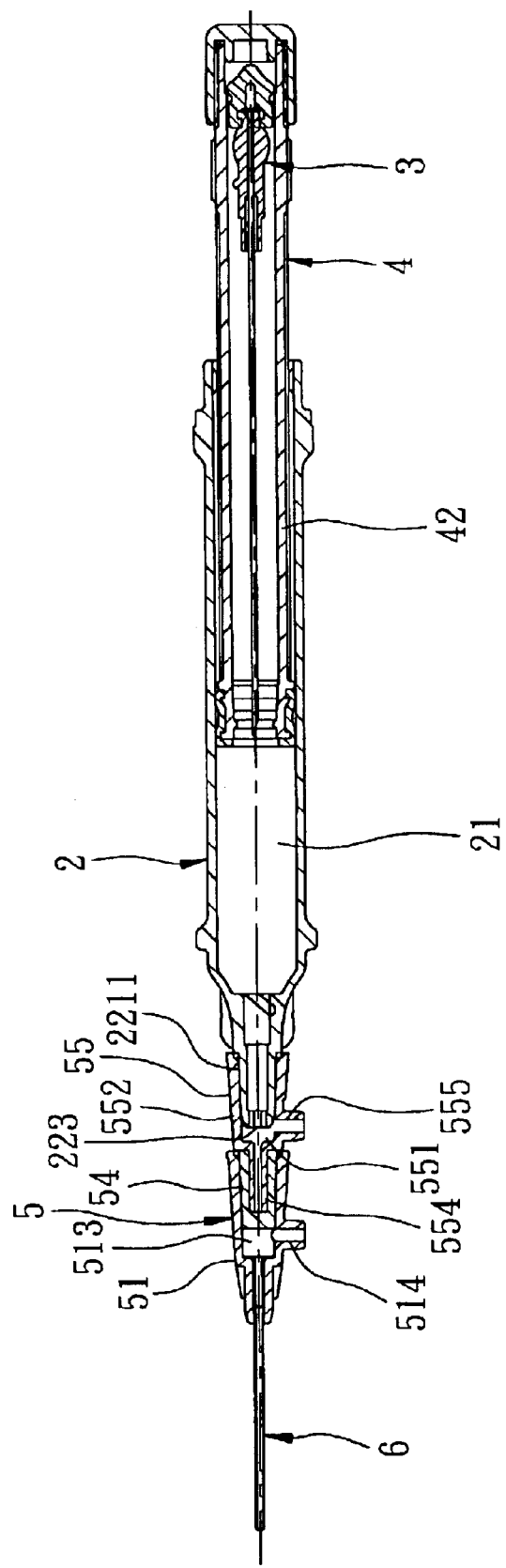
FIG. 11 is a sectional view of the third preferred embodiment of an intravenous catheter inserting device according to this invention.

Alternatively, referring to FIG. 11, the third preferred embodiment of the intravenous catheter inserting device according to this invention is shown to be similar to the first preferred embodiment in construction. The duct 513 of the catheter hub 5 is communicated with the passage 21 of the barrel 2 through a tubular insert 55. The tubular insert 55 has a front neck end 554 which is connected to a barrier member 54 and which confines a through way along the axis, and a rear flared end 552 which extends from the front neck end 554 along the first axis. The rear flared end 552 has an inner abutted surface which surrounds the first axis and which confines a fluid path 551, and a reentry port 555 which extends radially therethrough to communicate with the fluid path 551. The front surrounding region 2211 of the barrel 2 engages the inner abutted surface of the tubular insert 55. As such, in the same manner as that of the second preferred embodiment, after the used needle assembly 3 has been retracted into the plunger body 42, the slit in the barrier member 54 is closed by means of its elastomeric material property.

Figure 12:
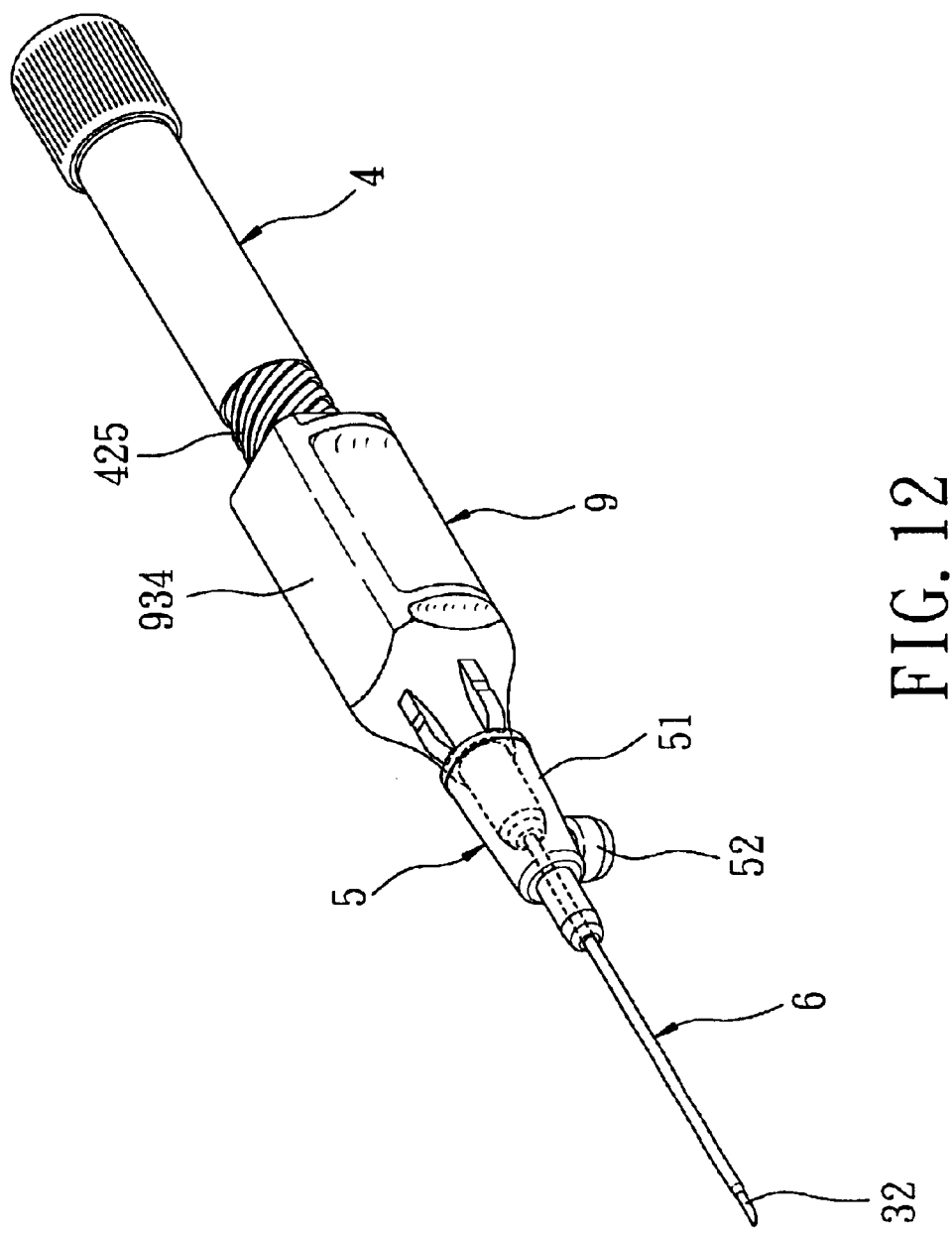
FIG. 12 is a perspective view of the fourth preferred embodiment of an intravenous catheter inserting device according to this invention.
Figure 13:
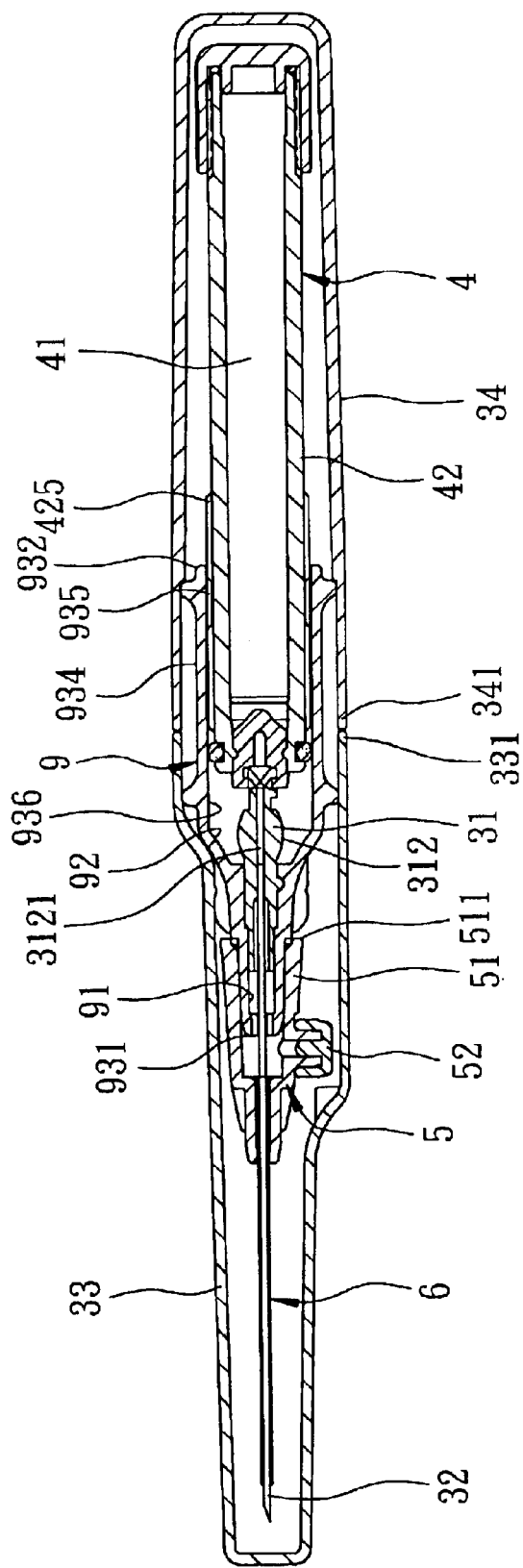
FIG. 13 is a sectional view of the fourth preferred embodiment of the intravenous catheter inserting device.

Referring to FIGS. 12 and 13, the fourth preferred embodiment of the intravenous catheter inserting device according to this invention is shown to include a barrel 9 which is shorter than that of the previous embodiments. The barrel 9 also has an inner surrounding barrel wall surface 936 which includes smaller-diameter and larger-diameter segments 91,92 and which confines a passage having open forward and rearward ends 931,932. The sleeve wall 511 of the catheter hub 5 is brought to engage the open forward end 931. The larger-diameter segment 92 has a male screw thread segment 935 so as to threadedly engage the female screw thread segment 425 formed on the outer plunger wall surface of the plunger 4. As such, in use, the health care worker can grasp the outer surrounding barrel wall surface 934 and insert the needle cannula 32, as well as the tubular catheter 6, into the patient's vein such that blood can flow into the barrel 9. Then, in the same manner described hereinabove, the needle cannula 32 can be retracted into the cavity 41 of the plunger 4 for safe disposal.

Furthermore, a tip protector 33 is disposed to shield the needle cannula 32 and the catheter hub 5, and has a larger open end 331 for insertion of a front half portion of the barrel 9. A sleeve tube 34 is disposed to shield the plunger 4, and has an open end 341 for insertion of a rear half portion of the barrel 9. Thus, the needle cannula 32 and the plunger 4 can be completely shielded by the tip protector 33 and the sleeve tube 34 so as to prevent the health care worker from coming into contact therewith.

As illustrated, the intravenous catheter inserting device of this invention has the following advantages:

1. After insertion of the needle cannula 32, by rotating the plunger body 42 in the clockwise direction relative to the larger-diameter segment 212, the used needle assembly 3 can be retracted into the cavity 41 of the plunger body 42, thereby facilitating safe disposal of the intravenous catheter inserting device.

2. Since the anchoring segment 312 of the tubular needle seat 31 is light-transmissible and has the convex surface 316, blood flowing through the axial through hole 3121 is visible to the health care worker in a magnified state.

3. After the used needle assembly 3 has been retracted into the cavity 41, the health care worker can directly pull the plunger body 42 for drawing blood into the passage 21 or the blood collecting member 7 without the need to remove the barrel 2 and the catheter hub 5, thereby reducing the possibility of the health care worker coming into contact with blood.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. An intravenous catheter device for use with a disposable syringe which includes a barrel having an inner surrounding barrel wall surface which confines a passage that extends in a longitudinal direction and that has open forward and rearward ends opposite to each other in the longitudinal direction, and an outer surrounding barrel wall surface which has a front surrounding region that is proximate to the open forward end, a needle cannula retractably received in the open forward end, and a plunger which is received in the passage to be movable in the longitudinal direction, which extends outwardly of the open rearward end so as to be manually operable, which has a cavity extending in the longitudinal direction and containing fluid at a reduced pressure, and which is coupled with the needle cannula within the passage such that the needle cannula will be retracted into the cavity once the needle cannula is subjected to a suction force that arises as a result of a pressure difference between the ambient air and the reduced pressure, said intravenous catheter device comprising:

a catheter hub including
 a surrounding tip wall which surrounds an axis, and which confines a through hole extending along the axis,
 a sleeve wall which is opposite to said surrounding tip wall along the axis, and which has an inner sleeve wall surface that surrounds the axis, and that confines an insert hole larger than said through hole, said inner sleeve wall surface being adapted to be secured relative to the front surrounding region of the outer surrounding barrel wall surface of the barrel so as to bring the passage into alignment with said through hole, and
 an intermediate tubular wall which is interposed between said surrounding tip wall and said sleeve wall, which confines a duct that communicates said insert hole with said through hole, and that is adapted for the needle cannula to pass through when said inner sleeve wall surface is secured relative to the front surrounding region of the outer surrounding barrel wall surface of the barrel, and which has a communicating port extending therethrough to communicate said duct with ambient air; and
a tubular catheter including a proximate segment which is disposed in said through hole and which extends along the axis to communicate with said duct, and a distal segment which extends from said proximate segment along the axis to project outwardly of said surrounding tip wall, and which is adapted to be sleeved on the needle cannula and to permit the needle cannula to extend outwardly thereof, when the needle cannula is brought to pass through said duct.

2. The intravenous catheter device according to claim 1, wherein said intermediate tubular wall has an inner tubular wall surface to confine said duct, and an outer tubular wall surface opposite to said inner tubular wall surface in radial directions, said inner tubular wall surface forming a retaining shoulder with said surrounding tip wall, said retaining shoulder confronting said duct along the axis, said proximate segment extending along the axis to project outwardly of said through hole and terminating at a flange portion which abuts against and which is retained at said retaining shoulder.

3. The intravenous catheter device according to claim 2, wherein said communicating port extends radially through said inner and outer tubular wall surfaces.

4. The intravenous catheter device according to claim 3, wherein said inner sleeve wall surface confines a boundary area which surrounds the axis, and has a reentry port which extends radially through said sleeve wall to communicate with said insert hole, and which is opposite to said communicating port relative to said boundary area, said intravenous catheter device further comprising:
 a barrier member which engages said inner sleeve wall surface at said boundary area; and
 a tubular insert which has a front neck end that is connected to said barrier member and that confines a through way along the axis, and a rear flared end that extends from said front neck end along the axis and that has an inner abutted surface, said inner abutted surface surrounding the axis and confining a fluid path which extends to communicate with said reentry port, said inner abutted surface being adapted to engage the front surrounding region of the outer surrounding barrel wall surface of the barrel, thereby aligning said through way with the passage of the barrel so as to permit the needle cannula to extend through said through way and outwardly of said tubular catheter.

5. The intravenous catheter device according to claim 4, wherein said barrier member is formed from an elastomeric material.

6. The intravenous catheter device according to claim 3, wherein said inner sleeve wall surface confines a boundary area which surrounds the axis,
 said intravenous catheter device further comprising:
 a barrier member which engages said inner sleeve wall surface at said boundary area; and
 a tubular insert which has a front neck end that is connected to said barrier member and that confines a through way along the axis, and a rear flared end that extends from said front neck end along the axis, said rear flared end having an inner abutted surface which surrounds the axis and which confines a fluid path, and a reentry port which extends radially to communicate with said fluid path and which is opposite to said communicating port relative to said boundary area, said inner abutted surface of said rear flared end being adapted to engage the front surrounding region of the outer surrounding barrel wall surface of the barrel, thereby aligning said through way with the passage of the barrel so as to permit the needle cannula to extend through said through way and outwardly of said tubular catheter.

7. An intravenous catheter inserting device comprising:
a catheter hub including
 a surrounding tip wall which surrounds a first axis, and which confines a through hole extending along the first axis,
 a sleeve wall which is opposite to said surrounding tip wall along the first axis, and which has an inner sleeve wall surface that surrounds the first axis, and that confines an insert hole larger than said through hole, and
 an intermediate tubular wall which is interposed between said surrounding tip wall and said sleeve wall, which confines a duct communicating said insert hole with said through hole, and which has a communicating port extending therethrough to communicate said duct with ambient air;
a tubular catheter including a proximate segment which is disposed in said through hole and which extends along the first axis to communicate with said duct, and a distal segment which extends from said proximate segment along the first axis to project outwardly of said surrounding tip wall;
a barrel having outer and inner surrounding barrel wall surfaces opposite to each other and surrounding a second axis, said inner surrounding barrel wall surface confining a passage having open forward and rearward ends that are disposed opposite to each other in a longitudinal direction parallel to the second axis, said inner surrounding barrel wall surface including a larger-diameter segment and a smaller-diameter segment that confine rear and front passageways, respectively, and that are disposed proximate to said open rearward and forward ends, respectively, to form a surrounding shoulder portion between said larger-diameter segment and said smaller-diameter segment, said outer surrounding barrel wall surface having a front surrounding region which is proximate to said open forward end, and which is secured relative to said inner sleeve wall surface, thereby resulting in coincidence of the first axis with the second axis;

a needle cannula including tip and fixed ends opposite to each other, and a middle segment interposed between said tip and fixed ends;

a tubular needle seat received in said passage and extending along the second axis, said tubular needle seat including
- a hub end disposed to secure said fixed end,
- a surrounding engaged wall which extends from said hub end along the second axis, and which confines an axial path to accommodate or communicate with said fixed end, said surrounding engaged wall having an outer engaged wall surface which surrounds the second axis, and which engages and which is rotatable relative to said smaller-diameter segment about the second axis between interengaged and released positions, where said surrounding engaged wall is unmovable and movable relative to said smaller-diameter segment along the second axis, respectively, and
- an anchoring segment which confines an axial through hole to communicate with said passage, and which extends outwardly of said front passageway from said surrounding engaged wall, said anchoring segment terminating at an anchoring end which is rotated with said surrounding engaged wall to move from a hook-up position that is closer to said surrounding shoulder portion, to a depressed position that is remote from said surrounding shoulder portion when said surrounding engaged wall is turned in a clockwise direction from the interengaged position to the released position; and a plunger received in said passage such that in a use position, said plunger is movable along said larger-diameter segment in the longitudinal direction, and such that in a disposal position, said plunger is unmovable along but is rotatable relative to the larger-diameter segment, said plunger including
- a plunger body which includes a top end wall disposed to confront said surrounding shoulder portion, and a bottom end wall opposite to said top end wall in the longitudinal direction, said bottom end wall extending outwardly of said open rearward end to permit movement and rotation of said plunger, said top end wall having an inner peripheral edge portion which surrounds the second axis, and which defines a cavity therein, said cavity extending along the second axis and towards said bottom end wall and containing fluid at a reduced pressure, and
- a seal member including
    - an anchored portion disposed to be engageable with said anchoring end such that when said plunger is in the disposal position and when said surrounding engaged wall is in the interengaged position, rotation of said plunger body in the clockwise direction relative to said larger-diameter segment brings said surrounding engaged wall to turn from the interengaged position to the released position, thereby moving said anchoring end from the hook-up position to the depressed position, and
    - a sealing portion which is sealingly attached to said inner peripheral edge portion along a sealing line so as to trap said fluid in said cavity, the sealing line being configured such that movement of said anchoring end from the hook-up position to the depressed position results in depression of said anchored portion so as to rip the sealing line, thereby releasing said seal member from said plunger body, so that said tubular needle seat together with said needle cannula will be pulled by said seal member which is suctioned into said cavity due to a pressure difference between the reduced pressure and the ambient air that is introduced through said communicating port, thereby permitting retraction of said needle cannula from said tubular catheter into said cavity.

8. The intravenous catheter inserting device according to claim 7, wherein said front surrounding region of said outer surrounding barrel wall surface of said barrel is inserted into said insert hole so as to abut against said inner sleeve wall surface of said sleeve wall of said catheter hub.

9. The intravenous catheter inserting device according to claim 8, wherein said plunger body has an outer plunger wall surface which surrounds the second axis, said intravenous catheter inserting device further comprising first male and female screw thread segments respectively disposed on said outer plunger wall surface and said larger-diameter segment to restrain said plunger body from displacing along said larger-diameter segment while permitting rotation of said plunger body in a clockwise direction relative to said larger-diameter segment in the disposal position.

10. The intravenous catheter inserting device according to claim 9, further comprising second male and female screw thread segments respectively disposed on said outer engaged wall surface and said smaller-diameter segment to permit rotation of said outer engaged wall surface relative to said smaller-diameter segment.

11. The intravenous catheter inserting device according to claim 10, wherein said anchoring segment is made of a material that is light transmissible so as to permit viewing of liquid, flowing through said axial through hole.

12. The intravenous catheter inserting device according to claim 11, wherein said anchoring segment is configured in such a manner so as to provide a magnified view of blood in said axial through hole.

13. The intravenous catheter inserting device according to claim 12, wherein said seal member is formed from an elastomeric material.

14. The intravenous catheter inserting device according to claim 13, wherein said anchored portion has an inner surrounding wall which extends along the second axis to confine a recess that is configured to accommodate said anchoring end, said intravenous catheter inserting device further comprising third male and female screw thread segments disposed respectively on said anchoring end and said inner surrounding wall so as to permit said anchored portion to be brought to engage with said anchoring end by virtue of rotation of said third male and female screw thread segments relative to each other.

15. The intravenous catheter inserting device according to claim 14, further comprising a surrounding protrusion disposed to extend from said inner peripheral edge portion in radial directions and towards the second axis so as to be in frictional contact with said sealing portion, thereby establishing the sealing line.

16. The intravenous catheter inserting device according to claim 15, further comprising a catcher portion disposed on said inner peripheral edge portion proximate to said bottom end wall and configured to prevent said tubular needle seat and said needle cannula from impinging upon said bottom end wall.

17. The intravenous catheter inserting device according to claim 7, wherein said inner sleeve wall surface confines a boundary area which surrounds the first axis, and has a reentry port which extends radially through said sleeve wall to communicate with said insert hole and which is opposite to said communicating port relative to said boundary area, said intravenous catheter inserting device further comprising:

a barrier member which engages said inner sleeve wall surface at said boundary area; and a tubular insert which has a front neck end that is connected to said barrier member and that confines a through way along the first axis, and a rear flared end that extends from said front neck end along the first axis and that has an inner abutted surface, said inner abutted surface surrounding the first axis and confining a fluid path which extends to communicate with said reentry port, said inner abutted surface engaging said front surrounding region of said outer surrounding barrel wall surface of said barrel, thereby aligning said through way with said passage of said barrel so as to permit said needle cannula to extend through said through way and outwardly of said tubular catheter.

* * * * *